United States Patent
Engel et al.

(10) Patent No.: US 10,964,092 B2
(45) Date of Patent: Mar. 30, 2021

(54) VISUALIZATION OF MEDICAL IMAGE DATA

(71) Applicant: Siemens Healthcare GmbH, Erlangen (DE)

(72) Inventors: Klaus Engel, Nuremberg (DE); Simone Hufnagel, Burgthann (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/814,298

(22) Filed: Mar. 10, 2020

(65) Prior Publication Data

US 2020/0302674 A1    Sep. 24, 2020

(30) Foreign Application Priority Data

Mar. 21, 2019   (EP) .................................... 19164362

(51) Int. Cl.
*G06T 15/06* (2011.01)
*A61B 5/055* (2006.01)
*A61B 5/00* (2006.01)
*A61B 6/02* (2006.01)
*A61B 6/03* (2006.01)
(Continued)

(52) U.S. Cl.
CPC .............. *G06T 15/06* (2013.01); *A61B 5/055* (2013.01); *A61B 5/7445* (2013.01); *A61B 6/025* (2013.01); *A61B 6/032* (2013.01); *A61B 6/466* (2013.01); *A61B 6/5294* (2013.01); *G06T 15/08* (2013.01); *G06T 19/20* (2013.01); *G06T 2210/41* (2013.01); *G06T 2219/2016* (2013.01)

(58) Field of Classification Search
None
See application file for complete search history.

(56) References Cited

U.S. PATENT DOCUMENTS

| | | | |
|---|---|---|---|
| 5,825,365 A | 10/1998 | Hirota et al. | |
| 2009/0174729 A1* | 7/2009 | Matsumoto | ............ G06T 15/08 345/619 |
| 2020/0054398 A1* | 2/2020 | Kovtun | ................... G06T 19/20 |

OTHER PUBLICATIONS

Kang D S et al: "An interactive exploded view generation using block-based re-rendering"; Medical Imaging 2011: Visualization, Image-Guided Procedures, and Modeling; SPIE; 1000 20th St. Bellingham WA 98225-6705 USA; pp: 1-7; Bd. 7964, Nr. 1; pp: 1-7; XP060008164; DOI: 10.1117/12.877895.
(Continued)

*Primary Examiner* — Edward Martello
(74) *Attorney, Agent, or Firm* — Harness, Dickey & Pierce, P.L.C.

(57) ABSTRACT

Described is a method for the visualization of medical image data as volume data. As part of the method, medical image data is acquired. A 3D mask is produced by segmenting the image data and classifying the segmented regions into predefined classes. Furthermore, the image data and the mask data are saved in two separate 3D texture files. A translation vector is then calculated, which describes the displacement of a segmented volume element between an original position and a destination position. In addition, a pictorial display of the image data is produced by applying a raycasting method to the stored image data. Finally, a displacement by the translation vector of a segmented volume element in the pictorial display is performed. A visualization entity is also described. Moreover, a medical imaging system is described.

13 Claims, 5 Drawing Sheets

(51) Int. Cl.
 *A61B 6/00* (2006.01)
 *G06T 15/08* (2011.01)
 *G06T 19/20* (2011.01)

(56) References Cited

OTHER PUBLICATIONS

Screen captures from YouTube video clip entitled "Cat Explorer", 6 pages, uploaded on Nov. 6, 2018 by user "Leap Motion". Retrieved from internet: https://www.youtube.com/watch?v=9KCA44GZRQg.

Subramanian N et al: "Volume rendering segmented data using 3D textures: a practical approach for intra-operative visualization"; Proceedings of the SPIE—The International Society for Optical Engineering SPIE—The International Society for Optical Engineering USA; Bd. 6141; 2006; pp. 61412Q-I; XP002793564; ISSN: 0277-786X.

Sonnet, Henry et al: "Integrating expanding annotations with a 3D explosion probe"; AVI '04 International Conference on Advanced Visual Interfaces; Gallipoli, Italy; May 25-28, 2004; Association for Computing Machinery, New York, NY, USA, May 25, 2004; pp. 63-70; XP058274606; DOI: 10.1145/989863.989871; ISBN: 978-1-58113-867-2; 2004.

Wilmot Li et al: "Automated generation of interactive 3D exploded view diagrams". ACM Transactions on Graphics, vol. 27. No. 3, pp. 1-7. XP058355394, ISSN: 0730-0301, DOI: 10.1145/1360612.1360700; Abstract; 2008.

Bruckner Stefan et al: "Exploded Views for Volume Data"; IEEE Transactions on Visualization and Computer Graphics; IEEE Service Center; Los Alamitos; CA; US; Bd. 12; Nr. 5; pp. 1077-1084; XP011150904; ISSN: 1077-2626; DOI: 10.1109/TVCG.2006.140.

European Search Report for European Patent Application No. 19164362 dated Aug. 30, 2019.

European Search Report for European Patent Application No. 19164362 dated Oct. 10, 2019.

* cited by examiner

VISUALIZATION OF MEDICAL IMAGE DATA

PRIORITY STATEMENT

The present application hereby claims priority under 35 U.S.C. § 119 to European patent application number EP 19164362.6 filed Mar. 21, 2019, the entire contents of which are hereby incorporated herein by reference.

FIELD

At least one embodiment of the invention generally relates to a method for the visualization of medical image data as volume data. As part of the method, medical image data is acquired. In addition to this, a three-dimensional mask is produced. For the purpose of producing the three-dimensional mask, the image data is segmented and the segmented regions are classified into predefined classes.

Furthermore, at least one embodiment of the invention generally relates to a visualization entity. The visualization entity comprises an acquisition unit for acquiring medical image data. Furthermore, the visualization entity has a mask production unit for producing a 3D mask by segmenting the image data and classifying the segmented regions into predefined classes.

Moreover, at least one embodiment of the invention generally relates to a medical imaging system. The medical imaging system comprises an image recording unit for producing image data from an examination region of an object to be examined.

BACKGROUND

Modern imaging methods are often employed to produce two-dimensional or three-dimensional image data, which can be used to visualize an examination object that is depicted and also for other applications. The image data obtained in this case, such as that produced by computer tomography or magnetic resonance imaging, is usually provided in the form of slice images for assessment by medical specialists.

However, three-dimensional image displays, also referred to as volume graphics, are also required for better illustration. The volumetric data required for such displays is visualized in three dimensions by means of so-called volume rendering in order to illustrate a case-specific anatomy. In this case, a volume region that has been captured as an image initially constitutes a unit, and therefore cannot readily be broken down into individual anatomical structures in order to assess these more precisely, for example.

The volume image display is based on the technique of so-called rendering. Image data is initially present as slice image data, wherein each voxel, at least in the case of computer tomography, is assigned a grayscale value corresponding to the density that has been determined at this location. However, this data cannot be converted directly into image data in the case of a three-dimensional perspective visualization, since the observation perspective and the position of the individual voxels relative to the observer must also be taken into consideration for such a visualization. Moreover, individual voxels each have only a single value initially, which provides e.g. information about the X-ray density in the case of CT imaging or about the content in respect of protons or hydrogen nuclei in the case of MR imaging, but they do not contain any information about the appearance of the respective material of a voxel, i.e. its color or whether it is highly reflective, for example. Each voxel of an observed volume is therefore assigned a texture. This procedure is also referred to as classification. A further step is concerned with the shading, i.e. how much light is reflected by a voxel in the direction of the observer and what color it has. Furthermore, a sampling step takes place for the purpose of sampling the volume. In this case, lines of sight are cast into the volume that is to be depicted. Once the interaction of the light with the volume has been calculated, the components along the line of sight are totaled and thus produce a pixel in the image.

Such an approach is realized by so-called raycasting, for example. However, it is not usually possible to display just one part of the volume data that has been produced.

Such a detailed visualization of subregions of the total recording region is nonetheless often desirable. In order to display anatomical details, use is conventionally made of so-called polygonal surface models. In this case, an artificially created model is used as a data basis for the visualization. As a result, each structure can be modeled individually and moved in the image independently of other structures. However, a surface display does not allow the interior of anatomical structures to be examined. For example, it is not possible to virtually cut an organ open and examine it for pathologies that might not be visible from the outside. Moreover, displays involving surface models require so-called intermediate representations, which have high data overheads and contribute to erroneous displays.

SUMMARY

At least one embodiment of the present invention is one allowing for a more accurate and simplified display of individual anatomical structures on the basis of three-dimensional image data from an examination region of an examination object.

Embodiments are directed to a method for the visualization of medical image data as volume data, a visualization entity, a medical imaging system, a computer program product and a computer-readable data medium in accordance with the independent claims.

At least one embodiment is directed to an inventive method for the visualization of medical image data as volume data, medical image data is first acquired from an object to be examined. For example, the image data may come from a medical imaging entity, e.g. a CT system or an MR system. The image data is then segmented, preferably automatically, and the segmented regions are classified into classes which typify predefined different organs or structure types. In this way, a mask is produced which assigns marks or labels to each of individual segmented volume elements in order to characterize them. Using these marks, a voxel can be assigned definitively to a specific organ type or tissue type. The image data and the mask data are stored in two separate 3D texture files. One of these texture files contains the information about the appearance of the individual voxel and the other file contains the information obtained from the segmentation or masking, indicating to which structure or to which organ a respective voxel must be attributed. The file for the "image data" comprises not only the density or concentration information produced by the medical imaging entities, but also volume texture data which more precisely defines the appearance of a voxel as briefly explained above. Furthermore, a translation vector is determined which describes the displacement of a segmented volume element between an original position and a destination position. The original position and the destination position can be predefined by a user with the aid of an input medium, for example. Moreover, a pictorial display of the image data is produced by applying a raycasting method to the stored image data. Furthermore, a displacement by the translation vector of a segmented volume element in the pictorial display takes place. In other words, the segmented volume element is displaced by the translation vector in the pictorial display. The displacement can be effected by a movement of the input medium, for example, the movement being controlled by the user. The displacement takes place in such a way that the image points in the destination region are produced by a sampling that is displaced by the translation vector, such that the image points in the destination region conserve the texture data of the original region. The displacement of volume data allows an improved illustration of subregions of the object to be examined.

At least one embodiment is directed to an inventive visualization of volumetric image data, in contrast to the use of polygonal surface models, also allows an illustration of the inner life of anatomical structures. This means that, for example, an organ can be virtually cut open and examined for pathological phenomena which are not visible externally. Moreover, the visualization of volume data does not require any intermediate representations, whereby the data overheads can be reduced and artifacts during the visualization can be avoided.

Moreover, the data overheads are reduced because, in spite of a translation of segments, only one and the same data set has to be held in the data store. Instead of changing textures in the data set, and therefore requiring increased storage space, the manipulation of the image data does not take place until the sampling for the visualization of the image data. Therefore the so-called rendering procedure can always be executed on the basis of the same data and the same routines irrespective whether and which displacement is performed. Moreover, only three different inputs are required for the displacement: the image data with a volume texture, a mask with labels for the segmentation, and a translation vector for the displacement of a segment.

At least one embodiment is directed to an inventive visualization entity including an acquisition unit for acquiring the medical image data. Part of the inventive visualization entity is also a mask production unit for producing a 3D mask by segmenting the image data and classifying the segmented regions into predefined classes. The inventive visualization entity also comprises a storage unit for storing the image data and the mask data in two separate 3D texture files.

At least one embodiment of the inventive medical imaging system comprises at least one embodiment of the inventive visualization entity and an image recording unit for producing image data from an examination region of an object to be examined.

At least one embodiment is directed to a method for visualization of medical image data as volume data, comprising:

acquiring the medical image data;

producing a 3D mask by segmenting the medical image data acquired and classifying segmented regions into defined classes;

respectively storing the medical image data and mask data of the 3D mask in two separate 3D texture files;

calculating a translation vector, describing displacement of a segmented volume element between an original position and a destination position;

producing a pictorial display of the medical image data by applying a raycasting method to the medical image data stored; and performing a displacement, using the translation vector calculated, of a segmented volume element in the pictorial display produced.

At least one embodiment is directed to a visualization entity, comprising:

an acquisition unit to acquire medical image data;

a mask production unit to produce a 3D mask by segmenting the medical image data acquired and to classify segmented regions into defined classes;

a storage unit to store the medical image data and mask data of the 3D mask in two separate 3D texture files;

a vector production unit to calculate a translation vector, describing displacement of a segmented volume element between an original position and a destination position;

a translation unit to perform the displacement using the translation vector of the segmented volume element; and a visualization unit to produce a pictorial display of the medical image data by applying a raycasting method to the medical image data stored.

At least one embodiment is directed to a medical imaging system, comprising:

the visualization entity of an embodiment; and an image recording unit to produce image data from an examination region of an object to be examined.

At least one embodiment is directed to a non-transitory computer program product storing a computer program, directly loadable into a storage unit of a medical imaging system, including program sections for executing the method of an embodiment when the computer program is executed in the medical imaging system.

At least one embodiment is directed to a non-transitory computer-readable medium, storing program sections, executable by a computer unit, to execute the method of the an embodiment when the program sections are executed by the computer unit.

To this extent, at least one embodiment is directed to a corresponding computer program product comprising a computer program that can be loaded directly into a storage entity of such a computer system, with program sections for executing all steps of at least one embodiment of the method for the visualization of medical image data as volume data when the computer program is executed in the computer system.

BRIEF DESCRIPTION OF THE DRAWINGS

The invention is explained again below on the basis of example embodiments and with reference to the appended figures, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewritable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewritable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewritable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewritable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment is directed to an inventive method for the visualization of medical image data as volume data, medical image data is first acquired from an object to be examined. For example, the image data may come from a medical imaging entity, e.g. a CT system or an MR system. The image data is then segmented, preferably automatically, and the segmented regions are classified into classes which typify predefined different organs or structure types. In this way, a mask is produced which assigns marks or labels to each of individual segmented volume elements in order to characterize them. Using these marks, a voxel can be assigned definitively to a specific organ type or tissue type. The image data and the mask data are stored in two separate 3D texture files. One of these texture files contains the information about the appearance of the individual voxel and the other file contains the information obtained from the segmentation or masking, indicating to which structure or to which organ a respective voxel must be attributed. The file for the "image data" comprises not only the density or concentration information produced by the medical imaging entities, but also volume texture data which more precisely defines the appearance of a voxel as briefly explained above. Furthermore, a translation vector is determined which describes the displacement of a segmented volume element between an original position and a destination position. The original position and the destination position can be predefined by a user with the aid of an input medium, for example. Moreover, a pictorial display of the image data is produced by applying a raycasting method to the stored image data. Furthermore, a displacement by the translation vector of a segmented volume element in the pictorial display takes place. In other words, the segmented volume element is displaced by the translation vector in the pictorial display. The displacement can be effected by a movement of the input medium, for example, the movement being controlled by the user. The displacement takes place in such a way that the image points in the destination region are produced by a sampling that is displaced by the translation vector, such that the image points in the destination region conserve the texture data of the original region. The displacement of volume data allows an improved illustration of subregions of the object to be examined.

At least one embodiment is directed to an inventive visualization of volumetric image data, in contrast to the use of polygonal surface models, also allows an illustration of the inner life of anatomical structures. This means that, for example, an organ can be virtually cut open and examined for pathological phenomena which are not visible externally. Moreover, the visualization of volume data does not require any intermediate representations, whereby the data overheads can be reduced and artifacts during the visualization can be avoided.

Moreover, the data overheads are reduced because, in spite of a translation of segments, only one and the same data set has to be held in the data store. Instead of changing textures in the data set, and therefore requiring increased storage space, the manipulation of the image data does not take place until the sampling for the visualization of the image data. Therefore the so-called rendering procedure can always be executed on the basis of the same data and the same routines irrespective whether and which displacement is performed. Moreover, only three different inputs are required for the displacement: the image data with a volume texture, a mask with labels for the segmentation, and a translation vector for the displacement of a segment.

At least one embodiment is directed to an inventive visualization entity including an acquisition unit for acquiring the medical image data. Part of the inventive visualization entity is also a mask production unit for producing a 3D mask by segmenting the image data and classifying the segmented regions into predefined classes. The inventive visualization entity also comprises a storage unit for storing the image data and the mask data in two separate 3D texture files.

In at least one embodiment, the inventive visualization entity also has a vector production unit for calculating a translation vector which describes the displacement of a segmented volume element between an original position and a destination position. The displacement or the translation vector can be specified e.g. by a movement of an input medium, the movement being controlled by the user, or by an original position and destination position of an input medium, the positions being selected by the user.

Moreover, at least one embodiment of the inventive visualization entity also has a translation unit for the displacement by the translation vector of the segmented volume element.

Part of at least one embodiment of the inventive visualization entity is also a visualization unit for producing a pictorial display of the image data by applying a raycasting method to the stored image data. The inventive visualization entity has the same advantages as the inventive method for the visualization of medical image data as volume data.

At least one embodiment of the inventive medical imaging system comprises at least one embodiment of the inventive visualization entity and an image recording unit for producing image data from an examination region of an object to be examined.

The image recording unit can be a CT scanning unit or an MR scanning unit or a tomosynthesis unit, for example.

At least one embodiment of the inventive medical imaging system has the same advantages as at least one embodiment of the inventive visualization entity.

Parts of at least one embodiment of the inventive visualization entity can be developed primarily in the form of software components. This relates in particular to parts of the acquisition unit, the mask production unit, the vector production unit, the translation unit and the visualization unit. In principle, some of these components can however also be realized in the form of programmable hardware, e.g. FPGAs or similar, especially if particularly rapid calculations are involved. Likewise, the necessary interfaces can also be developed as software interfaces, e.g. if only a transfer of data from other software components is involved. However, they can also be developed as hardware-based interfaces which are controlled by suitable software.

A realization that is partly software-based has the advantage that computer systems which are already being used in imaging systems, supplemented by hardware units for recording image data from the patient, can easily be upgraded by means of a software update in order to operate in the inventive manner.

To this extent, at least one embodiment is directed to a corresponding computer program product comprising a computer program that can be loaded directly into a storage entity of such a computer system, with program sections for executing all steps of at least one embodiment of the method for the visualization of medical image data as volume data when the computer program is executed in the computer system.

Such a computer program product may comprise further elements in addition to the computer program, e.g. documentation and/or further components, including hardware components such as e.g. hardware keys (dongles, etc.) for use of the software.

For the purpose of transportation to the storage entity of the computer system and/or storage at the computer system, use can be made of a computer-readable medium, e.g. a memory stick, a hard disc or any other transportable or built-in data medium on which are stored the program sections of the computer program that can be read in and executed by a computer unit. For this purpose, the computer unit may comprise e.g. one or more interacting microprocessors or similar.

The claims and the following description both contain particularly advantageous embodiments and developments of the invention. In this case, the claims in one class of claim can in particular also be developed in the same way as the dependent claims of another class of claim and the description parts thereof. In addition, the various features of different example embodiments and claims can also be combined within the context of the invention to form further example embodiments.

In a particularly preferred development of at least one embodiment of the inventive method for the visualization of medical image data as volume data, the segmented volume element is made transparent at the original position. A transparent effect can be achieved by zeroing a value of the opacity for the segmented volume element at the original position. Advantageously, the volume element to be displaced does not appear duplicated in the pictorial display. In this way, concealment of other structures at the original position is avoided in the pictorial display.

In an embodiment of the inventive method for the visualization of medical image data as volume data, a collider object is created for each segmented volume element, the shape of the collider object being adapted to the dimensions of the segmented volume element. Such a collider object is a structure that can be appended to a three-dimensional object. The collider object itself assumes the shape of the three-dimensional object and is responsible for registering, and transferring to other interfaces, any occurrence of a collision or contact of the three-dimensional object with other collider objects. Furthermore, the translation vector is determined from the difference between the current position of an input medium and the position at which the input medium first touches the collider object, and at the same time the user indicates a wish to displace the segmented volume element. Using this variant, it is possible to achieve a displacement effect for individual structures that are to be made prominent in a region to be examined.

In a specific embodiment of the inventive method for the visualization of medical image data as volume data, a distance between the segmented volume element to be displaced and the remaining volume is predefined, and the translation vector is derived from the product of a difference between a distance factor and the value 1, and a difference between a position of the center of the segmented volume element to be displaced at its starting position and a current position of an input medium. In this case, the length of the translation path depends on both a predefined distance factor and the distance between the input medium and the segment to be displaced. Individual anatomical structures can be brought out and given better visibility in this way. A type of exploded display of individual or multiple different anatomical structures can advantageously be achieved, and the anatomical structures can then be examined more closely in this display.

In a variant of at least one embodiment of the inventive method for the visualization of medical image data as volume data, segmented volume elements lying close to the input medium are displaced by a greater extent than segmented volume elements lying farther away from the input medium.

Figure 1:
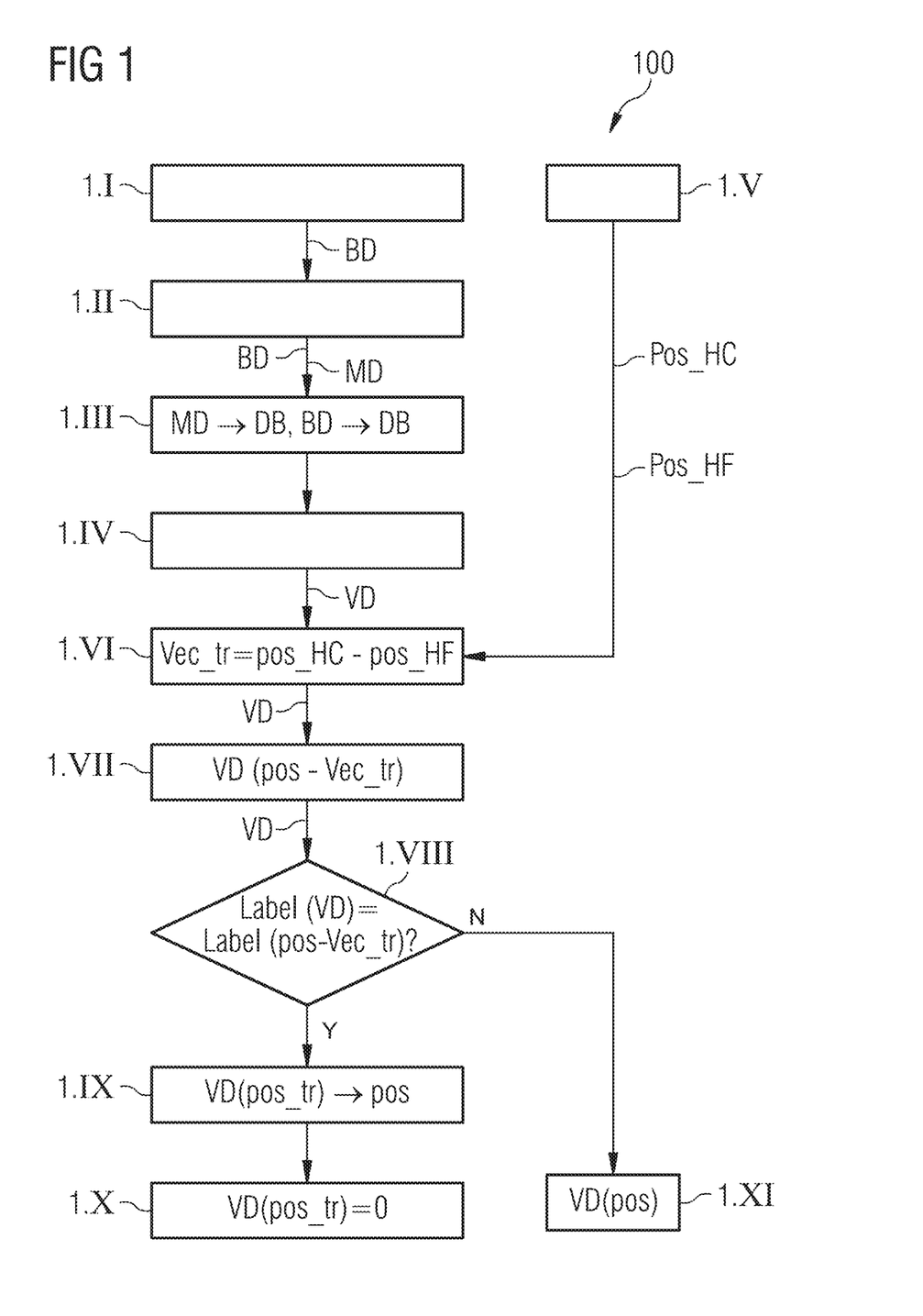
FIG. 1 shows a flow diagram illustrating a method for the visualization of medical image data as volume data according to an example embodiment of the invention.

FIG. 1 shows a flow diagram 100 illustrating a method for the visualization of medical image data as volume data according to an example embodiment of the invention. In the step 1.I, image data BD of a region to be examined of a patient is first received from a medical imaging entity. This image data BD is present in the form of grayscale values which vary according to location. The image data BD is segmented in the step 1.II. In other words, individual organs or other body structures are identified and differentiated from each other.

This procedure can be fully automated, partly automated, or performed by qualified staff who mark border lines in the image data BD, in order thus to classify the image data into segmented regions. As part of the segmentation, a 3D mask MD is created and regions in the image volume are assigned specific classes or tissue types. This mask allocates so-called labels to individual voxels, the labels definitively allocating a voxel to a segment or to a segment type. This results in two data sets, a volume data set containing the grayscale values of the image data BD and a mask data set MD containing the mask data which allocates each voxel to a specific segment or body part. The image data BD is also allocated texture information, which is derived from the knowledge of the optical features allocated to the individual organs or tissue types, e.g. the color or reflective effects thereof.

These two data sets BD, MD are saved as two separate textures or in two separate texture files in the step 1.III. In the step 1.IV following thereupon, a visualization of the image data as volume data VD is then performed by means of a raycasting method. As part of this raycasting method, virtual rays are directed into the image volume and an image of a region to be examined is produced on the basis of the sampled image data BD, the image being constructed from corresponding visualized volume data VD. In the visualized image, a user can now select and displace individual segments.

In order to achieve this, a segment to be displaced is selected by a user in the step 1.V with the aid of an input means, e.g. a hand or a so-called controller. The user points, e.g. using the input medium, to a structure to be displaced at a position pos_HF on an image display, at which position the structure to be displaced is located in the image, and indicates a wish to displace this structure. On the basis of the known position of the center of the structure to be displaced and the dimensions thereof in the image, a so-called collider object of the structure is now created, whose shape is adapted to the dimensions of the structure to be displaced. For this purpose, the center and the dimensions or boundaries of the selected segment are determined. This procedure can be performed with reference to the stored mask data MD, which allocates each image point to a segment. Furthermore, by moving the input medium to the destination position pos_HC, the user specifies the location in the visualized image volume to which the structure is to be displaced.

In the step 1.VI, a translation vector Vec_tr is determined on the basis of a displacement movement of a user. More precisely, it is calculated on the basis of the starting position pos_HF and the destination position pos_HC of the translation vector Vec_tr as follows:

$$\text{Vec}\_tr = \text{pos}\_HC - \text{pos}\_HF \quad (1).$$

Once the translation vector Vec_tr has been determined, the access to the texture coordinates is also adapted. For otherwise the density value or a texture of a sampling volume at a current sampling position pos would be visualized by reading out the image data BD and the allocated texture thereof at the current position pos. As a result of the translation by the translation vector Vec_tr, however, a position pos_tr=pos−Vec_tr which is displaced by the translation vector Vec_tr is sampled in the step 1.VII.

If the mask data MD at this position includes the label of the structure to be displaced, this being checked in the step 1.VIII and characterized by "Y" in FIG. 1, in the step 1.IX the sampling position pos is then assigned the density value or the texture data of the visualized volume data VD (pos_tr) and not that of the volume data VD (pos), such that the current texture coordinate at the location pos is changed in the visualized image. In the step 1.X, a change of the texture at the displaced position pos_tr is also effected, such that the structure to be displaced is transparent at the original position pos_tr. In this way, a duplicate display of the structure to be displaced is prevented.

If the displaced position pos_tr is not allocated a label of the structure to be displaced, as characterized by "N" in FIG. 1, in the step 1.XI the sampling position pos is assigned the density value of the original volume data VD (pos) and therefore no change of the visualized image takes place at this location. In other words, in this case the current sampling position pos is located outside the region of the structure to be displaced.

Figure 2:
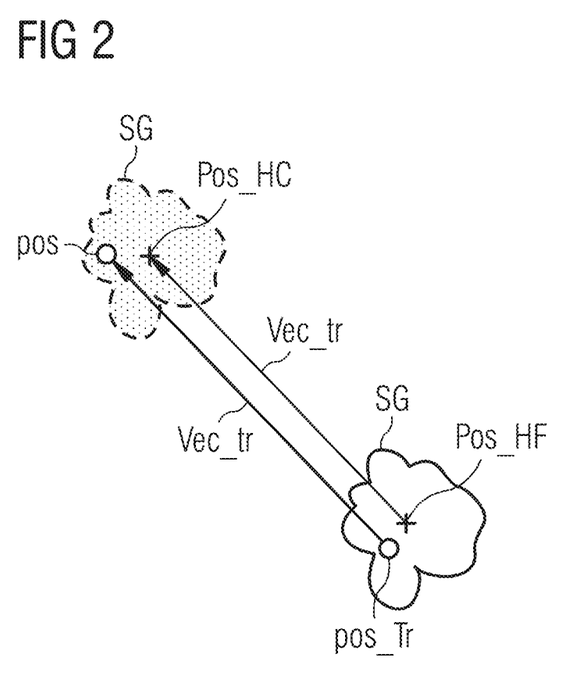
FIG. 2 shows a schematic display of a displacement of a segment of visualized volume data.

FIG. 2 illustrates a schematic display of a displacement of a segment SG of visualized volume data. The segment SG is to be displaced by the translation vector Vec_tr from the position pos_HF to the current position pos_HC. An image point at the location pos is now allocated not the texture of the position pos in the volume data, but the texture of the position pos_Tr as displaced by the translation vector Vec_tr. In this way, the structure SG to be displaced is displaced from the position pos_Tr to the location pos.

Figure 3:
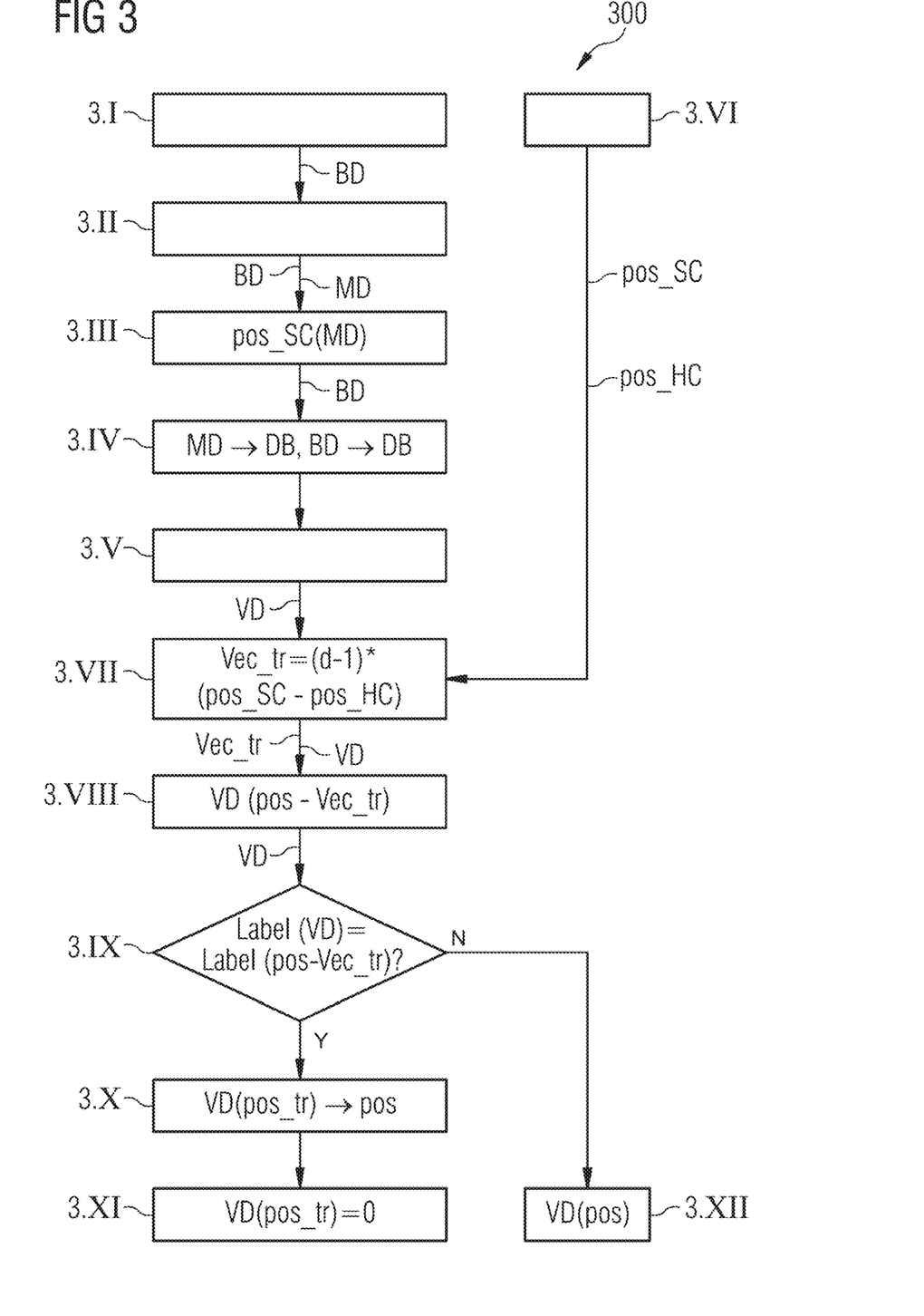
FIG. 3 shows a flow diagram illustrating a method for the visualization of medical image data as volume data according to an alternative example embodiment of the invention.

FIG. 3 shows a flow diagram which illustrates a method for the visualization of medical image data as volume data according to an alternative example embodiment of the invention. The example embodiment illustrated in FIG. 3 differs from the example embodiment illustrated in FIG. 1 essentially in that the translation vector Vec_tr is defined differently. In this way, by displacing a selected structure, the distance between the structures in the visualized image volume is magnified around the position of the input medium in a defined region, in a similar manner to an exploded diagram. Such a display allows individual structures to be assessed more precisely.

In the step 3.I, image data BD of a region to be examined of a patient is first received from a medical imaging entity as per the example embodiment illustrated in FIG. 1. This image data BD is present in the form of grayscale values, which vary according to location. The image data BD is segmented in the step 3.II. As part of the segmentation, a 3D mask MD is created and segmented regions in the image volume are assigned different classes or tissue types. The mask MD assigns so-called labels to individual voxels, the labels definitively allocating a voxel to a segment. This results in two data sets, an image data set BD containing the grayscale values of the image data and texture information, and a mask data set MD containing the mask data which allocates each voxel to a specific segment or body part.

In the step 3.III, the position pos_SC of the center of the respective structure is determined for each of the segments or structures. Such a center can be determined as a coordinate center of a segment, for example.

The image data set BD and the mask data set MD are then stored as two separate textures in the step 3.IV.

In the step 3.V, a visualization of volume data VD is then performed by means of a raycasting method, which was already briefly explained in connection with FIG. 1. In the visualized image, a user can now select and displace individual segments.

In the step 3.VI, a segment to be exposed is selected in the visualized display by the user with the aid of an input medium. For example, the user uses the input medium in order to come closer, from a specific direction, to the segment to be exposed, until a current position pos_HC is reached.

In the step 3.VII, a translation vector Vec_tr is determined. In the case of the example embodiment illustrated in FIG. 3, the structure selected by the user is then displaced from its center pos_SC by a distance that is specified by a predefined distance factor in the direction of the current position pos_HC of the input medium. The dimensionless distance factor dist can be selected without restriction in advance. For example, individual structures can all be displaced by the same factor, or structures lying close to the input medium can be displaced by a greater extent than structures situated farther away.

On the basis of the starting position or the center position pos_SC, the current position of the input medium pos_HC and the distance factor dist, the translation vector Vec_tr is now calculated as follows:

$$\text{Vec\_}tr = (\text{dist}-1)*(\text{pos\_}SC - \text{pos\_}HC) \quad (2).$$

Once the translation vector Vec_tr has been determined, the access to the texture coordinates is also adapted. For otherwise a texture of a sampling volume at a current sampling position pos would be visualized by reading out the image data BD at the current position pos. As a result of the translation by the translation vector Vec_tr, a position pos_tr=pos−Vec_tr which is displaced by the translation vector Vec_tr is sampled in the step 1.VIII.

If the mask data MD at this position includes the label of the structure to be displaced, this being checked in the step 1.IX, in the step 1.X the sampling position pos is then assigned the density value of the volume data VD (pos_tr) and not that of the volume data VD (pos), such that the current texture coordinate or the texture at the current location pos is changed in the visualized image. In the step 1.XI, a change of the texture at the displaced position pos_tr is also effected, such that the structure to be displaced is transparent at the original position. In this way, a duplicate display of the structure to be displaced is prevented.

If the displaced position pos_tr is not allocated a label of the structure to be displaced, in the step 1.XII the sampling position pos is assigned the density value of the original volume data VD (pos) and therefore no change of the visualized image takes place at this location. In other words, in this case the current sampling position pos is located outside the region of the structure to be displaced.

Figure 4:
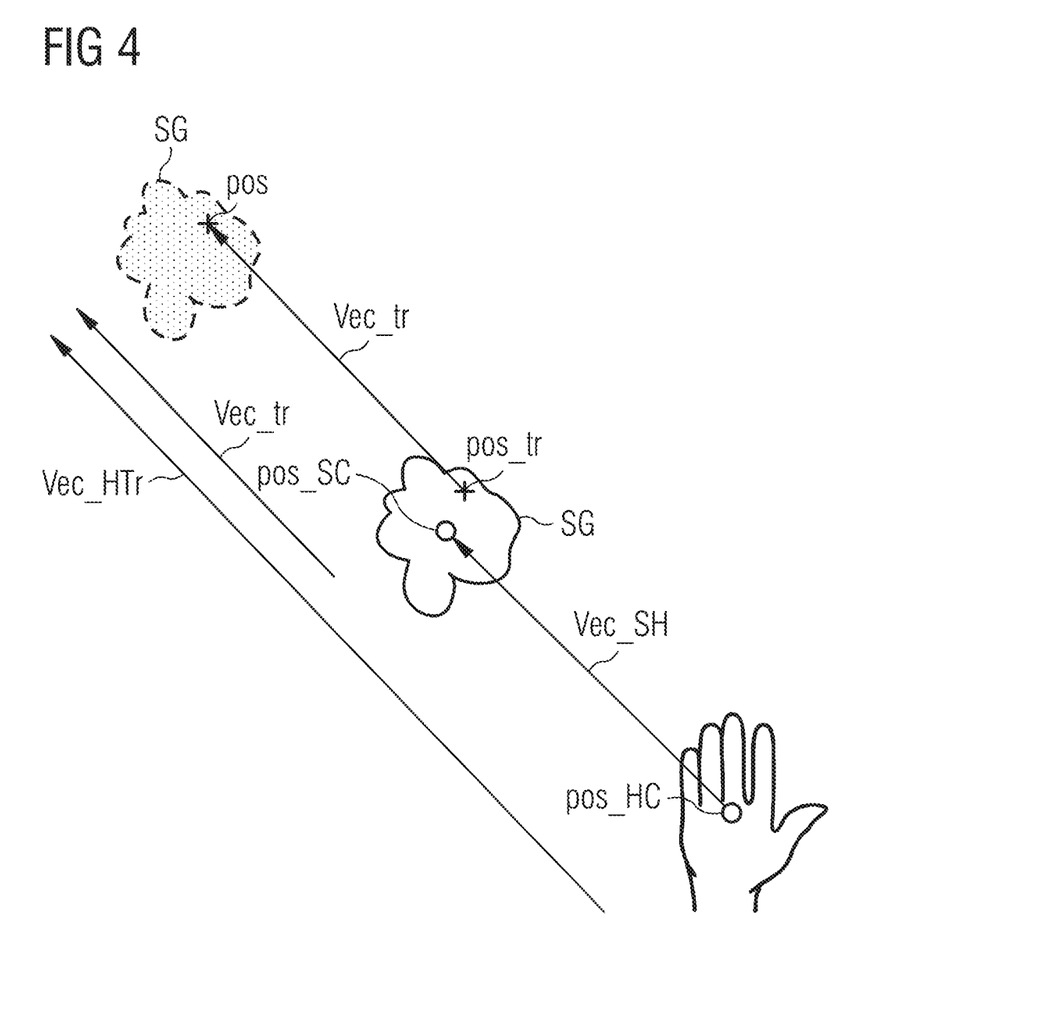
FIG. 4 shows a schematic display of a displacement of a segment of visualized volume data in the alternative example embodiment.

FIG. 4 shows a schematic display of a displacement of a segment of visualized volume data in the alternative example embodiment illustrated in FIG. 3.

The segment SG is to be displaced by the translation vector Vec_tr from the position pos_SC to the current position. An image point at the location pos is now allocated not the texture of the position pos in the volume data, but the texture of the position pos_Tr which is displaced by the translation vector Vec_tr. In this way, the structure SG to be displaced is displaced from the original position pos_SC to the current location. The vector Vec_SH between input medium and structure SG at the original position is calculated as follows:

$$\text{Vec\_}SH = \text{pos\_}SC - \text{pos\_}HC \quad (3).$$

A further vector, the vector Vec_HTr between hand and displaced position of the structure SG, is calculated as follows:

$$\text{Vec\_}HTr = \text{dist}*(\text{pos\_}SC - \text{pos\_}HC) \quad (4).$$

Figure 5:
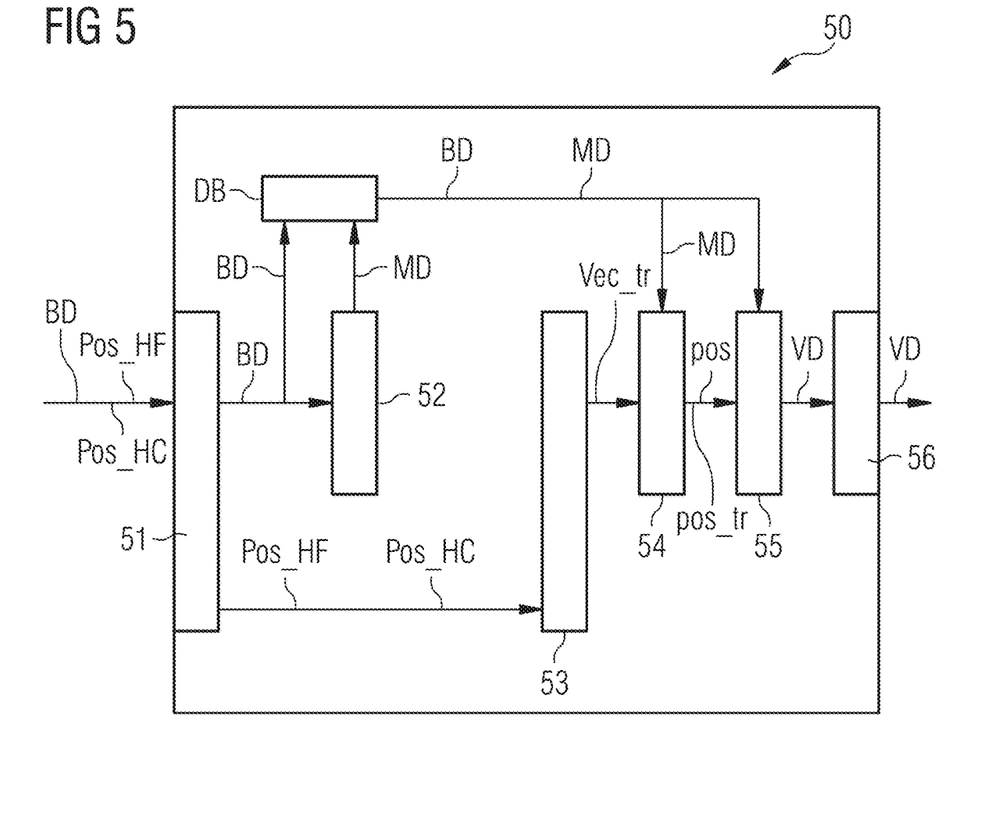
FIG. 5 shows a schematic display of a visualization entity according to an example embodiment of the invention.

FIG. 5 shows a schematic display of a visualization entity 50 according to an example embodiment of the invention.

The visualization entity 50 has an input interface 51 as an acquisition unit. The input interface 51 receives image data BD of a region to be examined of a patient from a medical imaging entity (not shown). The image data BD is required as volume data VD for the visualization of the region to be examined. Furthermore, the input interface 51 also receives data relating to the current position pos_HC of the input medium and the starting position pos_HF of the input medium. The image data BD is transferred to a mask production unit 52, which segments the image data BD relating to individual organs or other body structures and produces a mask that comprises mask data MD for all segmented structures. The mask data MD assigns specific classes or tissue types to segmented regions in the image volume. In this case, individual voxels are assigned so-called labels, which definitively allocate a voxel to a type of segment. This results in two data sets, a volume data set containing the grayscale values of the image data BD and corresponding texture data, and a mask data set MD containing the mask data which allocates each voxel to a specific segment or body part.

The two data sets BD, MD are temporarily stored in a data store DB, which is likewise part of the visualization entity 50. The visualization entity 50 also comprises a vector production unit 53, which calculates a translation vector Vec_Tr according to equation (1) or equation (2) on the basis of the data received from the input interface 51 relating to the current position pos_HC of the input medium and the starting position pos_HF of the input medium. The data of the translation vector Vec_Tr is transferred to a translation unit 54, which is likewise part of the visualization entity 50. The translation unit 54 determines a translation position pos_tr on the basis of the translation vector Vec_Tr and receives labels MD allocated to this translation position pos_tr from the data store, in order to determine whether a volume segment of the type of the volume segment SG to be displaced is present at the translation position pos_tr.

The type of the volume segment to be displaced is derived from the label at the starting position pos_HF. If this is the case, the translation position pos_tr is transferred to a visualization unit 55, which is likewise part of the visualization entity 50, as a sampling position. The visualization unit 55 is likewise part of the visualization entity 50. If no volume segment of the type of the volume segment SG to be displaced is present at the translation position pos_tr, the translation unit 54 forwards the original sampling position pos to the visualization unit 55 and the raycasting takes place at the original sampling position pos.

The visualization unit 55 also obtains the image data BD and mask data MD stored in the data store DB. On the basis of the received data BD, MD and the sampling position pos, pos_tr received from the translation unit, the visualization unit 55 produces a perspective pictorial display of the region to be examined with the aid of a raycasting method. The information relating to the translation vector Vec_tr and the translation position pos_tr is used by the visualization unit 55, during the raycasting method in the region of the volume segment SG to be displaced, to access the image data BD or textures allocated thereto in such a way that a desired displacement of the structure encompassed by the volume segment SG is achieved. The visualized volume data VD is transferred to an output interface 56, which forwards this data VD to an image display unit (not shown).

Figure 6:
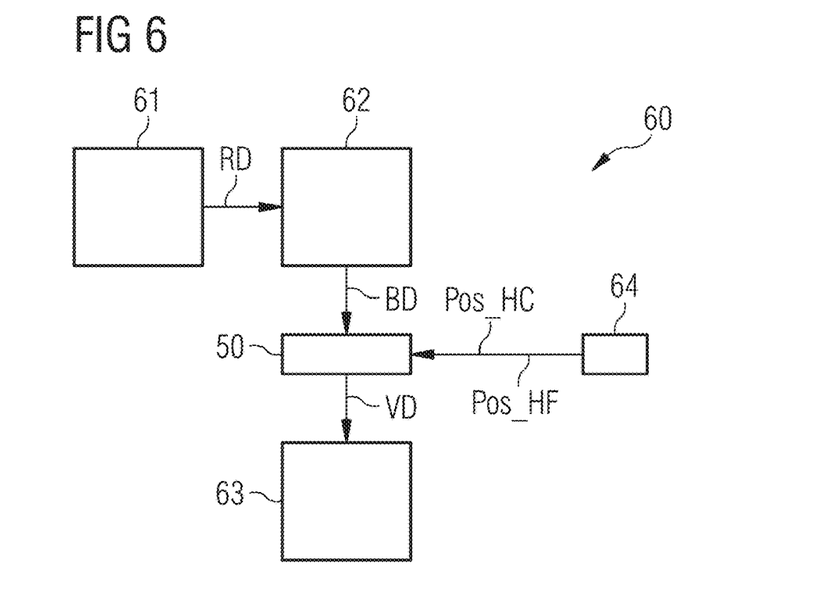
FIG. 6 shows a schematic display of a medical imaging system according to an example embodiment of the invention.

FIG. 6 illustrates a schematic display of a medical imaging system 60 according to an example embodiment of the invention. The medical imaging system 60 has a scanning unit 61, which is used to acquire raw data RD from an examination region of a patient. The scanning unit may comprise e.g. a scanning unit that is based on the principle of computer tomography. The raw data RD acquired by the scanning unit 61 is transferred to a control unit 62, which is used both to control the scanning unit 61 and to evaluate the raw data RD and reconstruct image data BD. The image data BD that is produced is transferred to a visualization entity 50, which has the structure shown in FIG. 5. The visualization entity 50 can also be controlled via an input unit 64, e.g. in order to transfer position data Pos_HC, Pos_HF of segments to be displaced, in image data BD that is to be visualized, to the visualization entity 50. The visualization data or visualized volume data VD produced by the visualization entity 50 is transferred to an image display entity 63, which comprises e.g. a monitor by means of which the visualized data VD can be pictorially displayed.

In conclusion, it is again noted that the method and devices described above are merely preferred example embodiments of the invention, and that the invention may be varied by a person skilled in the art without thereby departing from the scope of the invention as specified in the claims. For the sake of completeness, it is also noted that the use of the indefinite article "a" or "an" does not exclude the possibility that multiple instances of the features concerned may be present. Equally, the term "unit" dos not exclude the possibility that this may consist of multiple components, which can also be spatially distributed if applicable.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualization of medical image data as volume data, comprising:
   acquiring the medical image data;
   producing a 3D mask by segmenting the medical image data acquired and classifying segmented regions into defined classes;
   respectively storing the medical image data and mask data of the 3D mask in two separate 3D texture files;
   calculating a translation vector, describing displacement of a segmented volume element between an original position and a destination position;
   producing a pictorial display of the medical image data by applying a raycasting method to the medical image data stored; and
   performing a displacement, using the translation vector calculated, of a segmented volume element in the pictorial display produced.

2. The method of claim 1, wherein the segmented volume element is made transparent at an original position.

3. The method of claim 2, wherein
   a collider object is created for each segmented volume element, a respective shape of the collider object being adapted to dimensions of each respective segmented volume element,
   the translation vector is calculated from a difference between a current position of an input medium and a position at which the input medium first touches the collider object, and, a user, at a same time, being able to indicate a desire to displace the segmented volume element.

4. The method of claim 2, wherein
   a distance between the segmented volume element to be displaced and a remaining volume is defined, and
   the translation vector is calculated from a product of a difference between the distance and a value 1, and a difference between a position of a center of the segmented volume element to be displaced and a current position of an input medium.

5. The method of claim 4, wherein segmented volume elements lying relatively close to the input medium are displaced by a relatively greater extent than segmented volume elements lying relatively farther away from the input medium.

6. The method of claim 1, wherein
   a collider object is created for each segmented volume element, a respective shape of the collider object being adapted to dimensions of each respective segmented volume element,
   the translation vector is calculated from a difference between a current position of an input medium and a position at which the input medium first touches the collider object, and, a user, at a same time, being able to indicate a desire to displace the segmented volume element.

7. The method of claim 1, wherein
a distance between the segmented volume element to be displaced and a remaining volume is defined, and
the translation vector is calculated from a product of a difference between the distance and a value 1, and a difference between a position of a center of the segmented volume element to be displaced and a current position of an input medium.

8. The method of claim 7, wherein segmented volume elements lying relatively close to the input medium are displaced by a relatively greater extent than segmented volume elements lying relatively farther away from the input medium.

9. A non-transitory computer program product storing a computer program, directly loadable into a storage unit of a medical imaging system, including program sections for executing the method of claim 1 when the computer program is executed in the medical imaging system.

10. A non-transitory computer-readable medium, storing program sections, executable by a computer unit, to execute the method of the claim 1 when the program sections are executed by the computer unit.

11. A visualization entity, comprising:
an acquisition unit to acquire medical image data;
a mask production unit to produce a 3D mask by segmenting the medical image data acquired and to classify segmented regions into defined classes;
a storage unit to store the medical image data and mask data of the 3D mask in two separate 3D texture files;
a vector production unit to calculate a translation vector, describing displacement of a segmented volume element between an original position and a destination position;
a translation unit to perform the displacement using the translation vector of the segmented volume element; and
a visualization unit to produce a pictorial display of the medical image data by applying a raycasting method to the medical image data stored.

12. A medical imaging system, comprising:
the visualization entity of claim 11; and
an image recording unit to produce image data from an examination region of an object to be examined.

13. The medical imaging system of claim 12, wherein the image recording unit includes a scanning unit including one of:
a CT scanning unit,
an MR scanning unit, or
a tomosynthesis unit.

* * * * *